United States Patent [19]

Peferoen et al.

[11] Patent Number: 5,723,756
[45] Date of Patent: Mar. 3, 1998

[54] BACILLUS THURINGIENSIS STRAINS AND THEIR GENES ENCODING INSECTICIDAL TOXINS

[75] Inventors: Marnix Peferoen, Ghent; Bart Lambert, Beernem; Katrien Van Audenhove, Brugge, all of Belgium

[73] Assignee: Plant Genetic Systems, N.V., Ghent, Belgium

[21] Appl. No.: 443,679

[22] Filed: May 18, 1995

Related U.S. Application Data

[62] Division of Ser. No. 952,755, Nov. 17, 1992, Pat. No. 5,466,597.

[30] Foreign Application Priority Data

Apr. 26, 1990 [GB] United Kingdom ............... 90401144
Dec. 20, 1990 [GB] United Kingdom ............... 90403724

[51] Int. Cl.$^6$ ............... A01H 5/00; C12N 5/04; C12N 15/32; C12N 15/82
[52] U.S. Cl. ............... 800/205; 800/250; 435/69.1; 435/172.3; 435/410; 536/23.71
[58] Field of Search ............... 800/205, 250; 435/69.1, 172.3, 240.4, 410, 418, 419; 536/23.71

[56] References Cited

FOREIGN PATENT DOCUMENTS

| 0 142 924 | 5/1985 | European Pat. Off. . |
| 0 213 818 | 3/1987 | European Pat. Off. . |
| 0 269 601 | 6/1988 | European Pat. Off. . |
| 0 289 479 | 11/1988 | European Pat. Off. . |
| 0 305 275 | 3/1989 | European Pat. Off. . |
| 0 337 604 | 10/1989 | European Pat. Off. . |
| 0 340 197 | 11/1989 | European Pat. Off. . |
| 89/01515 | 2/1989 | WIPO . |
| 90/06999 | 6/1990 | WIPO . |
| 90/09445 | 8/1990 | WIPO . |

OTHER PUBLICATIONS

*Chemical Abstracts*, vol. 109, No. 5, Aug. 1, 1988, "Insect Resistance in Transgenic Plants Expressing *Bacillus Thuringiensis* Toxin Genes", p. 176, Abstract No. 33142v.

*Chemical Abstracts*, vol. 109, No. 17, Oct. 24, 1988, "Engineering of Insect Resistant Plants Using a B. thuringiensis Gene", pp. 211–212, Abstract No. 143900y.

*Microbiological Reviews*, vol. 53, No. 2, Jun. 1989, pp. 242–255, "Insecticidal Crystal Proteins of *Bacillus thuringiensis*", Herman Hofte, et al.

*Nucleic Acids Research*, vol. 18, No. 5, Dec. 19, 1989, "Nucleotide Sequence of a Coleopteran–Active Toxin Gene from a New Isolate of *Bacillus thuringiensis* susp. tolworthi", Aug. Sick, et al.

*Journal of Biochemistry*, vol. 270, pp. 133–136, "The Construction of *Bacillus thurigiensis* Strains Expressing Novel Entromicidal δ–Endotoxin Combinations", Neil Crickmore, et al.

*Proc. Natl. Acad. Sci.*, vol. 88, pp. 3324–3328, Apr. 1991, "Modification of Coding Sequence Enhances Plant Expression of Insect Control Protein Genes", Frederick J. Perlak, et al.

MacIntosh et al. (1990) J. of Invertebrate Pathology 56: 258–266.

*Primary Examiner*—Elizabeth McElwain
*Attorney, Agent, or Firm*—Burns, Doane, Swecker & Mathis, LLP

[57] ABSTRACT

Two new *Bacillus thuringiensis* strains, which are deposited at the DSM under accession numbers 5870 and 5871, produce new crystal proteins during sporulation that are toxic to Coleoptera and that are encoded by new genes. The crystal proteins contain protoxins, which can yield toxins as trypsin-digestion products. A plant, the genome of which is transformed with a DNA sequence that comes from either one of the strains and encodes an insecticidally effective portion of its respective protoxin or encodes its respective toxin, is resistant to Coleoptera. Each strain, itself, or its crystals, crystal proteins, protoxin, toxin and/or insecticidally effective protoxin portion can be used as the active ingredient in an insecticidal composition for combatting Coleoptera.

6 Claims, 3 Drawing Sheets

BACILLUS THURINGIENSIS STRAINS AND THEIR GENES ENCODING INSECTICIDAL TOXINS

This application is a divisional of application Ser. No. 07/952,755, filed Nov. 17, 1992 now U.S. Pat. No. 5,466,597.

BACKGROUND OF THE INVENTION (i) Field of the Invention

This invention relates to two new strains of *B. thuringiensis* (the "BtI109P strain" and the "BtI260 strain"), each of which produces crystallized proteins (the "BtI109P crystal proteins" and the "BtI260 crystal proteins", respectively) which are packaged in crystals (the "BtI109P crystals" and the "BtI260 crystals", respectively) during sporulation. The BtI109P and BtI260 strains were deposited under the provisions of the Budapest Treaty at the Deutsche Sammlung Für Mikroorganismen and Zellkulturen ("DSM"), Mascheroder Weg 1B, D-3300 Braunschweig, Federal Republic of Germany, under accession numbers 5870 and 5871, respectively, on Apr. 4, 1990.

This invention also relates to an insecticide composition that is active against Coleoptera and that comprises the BtI109P or BtI260 strain, as such, or preferably the BtI109P or BtI260 crystals, crystal proteins or the active component(s) thereof as an active ingredient.

This invention further relates

1) The "btI109P gene", from the genome of the BtI109P strain, which encodes an insecticidal protein (the "BtI109P protoxin") that is found in the BtI109P crystals; and 2) The "btI260 gene", from the genome of the BtI260 strain, which encodes an insecticidal protein (the "BtI260 protoxin") that is found in the BtI260 crystals.

The BtI109P and BtI260 protoxins are the proteins that are produced by their respective BtI109P and BtI260 strains before being packaged into their respective BtI109P and BtI260 crystals.

This invention still further relates to the "BtI109P toxin" and the "BtI260 toxin" which can be obtained (e.g., by trypsin digestion) from the BtI109P protoxin and the BtI260 protoxin, respectively. The BtI109P and BtI260 toxins are insecticidally active proteins which can be liberated from the BtI109P crystals and the BtI260 crystals, respectively, produced by the BtI109P strain and the BtI260 strain, respectively. Each toxin has a high activity against Coleoptera. The BtI109P and BtI260 toxins are believed to represent the smallest portions of their respective BtI109P and BtI260 protoxins which are insecticidally effective against Coleoptera.

This invention yet further relates to a chimaeric gene that can be used to transform a plant cell and that contains:

1) a part of the btI109P or btI260 gene (the "insecticidally effective btI109P or btI260 gene part") encoding an insectidicidally effective portion of the respective BtI109P or BtI260 protoxin, preferably a truncated part of the btI109P or btI260 gene (the "truncated btI109P or btI260 gene") encoding just the respective BtI109P or BtI260 toxin;

2) a promoter suitable for transcription of the insecticidally effective btI109P or btI260 gene part in a plant cell; and 3) suitable 3' end transcript formation and polyadenylation signals for expressing the insecticidally effective btI109P or btI260 gene part in a plant cell.

This chimaeric gene is hereinafter generally referred to as the "btI109P or btI260 chimaeric gene." Preferably, the insecticidally effective btI109P or btI260 gene part is present in the btI109P or btI260 chimaeric gene as a hybrid gene comprising a fusion of the truncated btI109P or btI260 gene and a selectable marker gene, such as the neogene (the "btI109P-neo or btI260-neo hybrid gene") encoding a BtI109P-NPTII or BtI260-NPTII fusion protein.

This invention also relates to:

1) a cell (the "transformed plant cell") of a plant, such as potato or corn, the nuclear genome of which is transformed with the insecticidally effective btI109P or btI260 gene part; and 2) a plant (the "transformed plant") which is regenerated from the transformed plant cell or is produced from the so-regenerated plant, the nuclear genome of which contains the insecticidally effective btI109P or btI260 gene part and which is resistant to Coleoptera.

This invention still further relates to a *B. thuringiensis* ("Bt") strain transformed, preferably by electroporation, with a vector carrying all or part of the btI109P or btI260 gene.

(ii) Description of Related Art

*B. thuringiensis* ("Bt") is a gram-positive bacterium which produces endogenous crystals upon sporulation. The crystals are composed of proteins which are specifically toxic against insect larvae. Three different Bt pathotypes have been described: pathotype A that is active against Lepidoptera, e.g., caterpillars; pathotype B that is active against certain Diptera, e.g., mosquitos and black flies; and pathotype C that is active against Coleoptera, e.g., beetles (Ellar et al, 1986).

A Bt strain, whose crystals are toxic to Coleoptera, has been described as Bt tenebrionis (U.S. Pat. No. 4,766,203; European patent publication ("EP") 149,162), as Bt M-7 or Bt San Diego (EP 213,818; U.S. Pat. No. 4,771,131) and as BtS1 (European patent application ("EPA") 88402115.5). Two other strains toxic to Coleoptera, BtPGSI208 and BtPGSI245, have also been described (PCT publication WO 90/09445).

The fact that conventional submerged fermentation techniques can be used to produce Bt spores on a large scale makes Bt bacteria commercially attractive as a source of insecticidal compositions.

Gene fragments from some Bt strains, encoding insecticidal proteins, have heretofore been identified and integrated into plant genomes in order to render the plants insect-resistant. However, obtaining expression of such Bt gene fragments in plants is not a straightforward process. To achieve optimal expression of an insecticidal protein in plant cells, it has been found necessary to engineer each Bt gene fragment in a specific way so that it encodes a water-soluble part of a Bt protoxin that retains substantial toxicity against its target insects (EPA 86300291.1 and EPA 88402115.5; U.S. patent application Ser. No. 821,582, filed Jan. 22, 1986).

SUMMARY OF THE INVENTION

In accordance with this invention, the two new Bt strains of pathotype C, i.e., the BtI109P and BtI260 strains, are provided. The BtI109P and BtI260 crystals, crystal proteins, protoxins and toxins, produced by the respective strains during sporulation, as well as insecticidally effective portions of the BtI109P and BtI260 protoxins, each possess insecticidal activity and can therefore be formulated into insecticidal compositions against Coleoptera in general, especially against *Agelastica alni, Diabrotica luteold, Haltica tombacina, Anthonomus grandis, Tenebrio molitor, Diabrotica undecimpunctata, Triboleum castaneum, Dicladispa armigera, Trichispa serica, Oulema oryzae,*

Colaspis brunnea, Lissorhorptrus oryzophilus, Phyllotreta cruciferae, Phyllotreta strtolata, Psylliodes punctulata, Entomoscelis americana, Meligethes aeneus, Ceutorynchus sp., Psylliodes chrysocephala, and Phyllotreta undulata and particularly against the Colorado potato beetle, Leptinotarsa decemlineata, which is a major pest of economically important crops.

Also in accordance with this invention, a plant cell genome is transformed with the insecticidally effective btI109P or btI260 gene part, preferably the truncated btI109P or btI260 gene. It is preferred that this transformation be carried out with the btI109P or btI260 chimaeric gene. The resulting transformed plant cell can be used to produce a transformed plant in which the plant cells in some or all of the plant tissues: 1) contain the insecticidally effective btI109P or btI260 gene part as a stable insert in their genome and 2) express the insecticidally effective btI109P or btI260 gene part by producing an insecticidally effective portion of its respective BtI109P or BtI260 protoxin, preferably its respective BtI109P or BtI260 toxin, thereby rendering the plant resistant to Coleoptera. The transformed plant cells of this invention can also be used to produce, for recovery, such insecticidal Bt proteins.

Further in accordance with this invention, a process is provided for rendering a plant resistant to Coleoptera by transforming the plant cell genome with the insecticidally effective btI109P or btI260 gene part, preferably the truncated btI109P or btI260 gene. In this regard, it is preferred that the plant cell be transformed with the btI109P or btI260 chimaeric gene.

Still further in accordance with this invention, there are provided the BtI109P and BtI260 protoxins, the insecticidally effective portions of such protoxins and the BtI109P and BtI260 toxins, as well as the btI109P and btI260 genes, the insecticidally effective btI109P and btI260 gene parts, the truncated BtI109P and btI260 genes and the chimaeric btI109P and btI260 genes.

Yet further in accordance with this invention, a Bt strain is transformed, preferably by electropotation, with a vector carrying all or part of the btI109P or btI260 gene encoding all or an insecticidally effective portion of the BtI109P or BtI260 protoxin.

Also in accordance with this invention are provided an insecticidal composition against Coleoptera and a method for controlling Coleoptera with the insecticidal composition, wherein the insecticidal composition comprises the BtI260 or BtI109P strain, crystals, crystal proteins, protoxin, toxin and/or insecticidally effective protoxin portions.

DETAILED DESCRIPTION OF PREFERRED EMBODIMENTS

Figure 1:
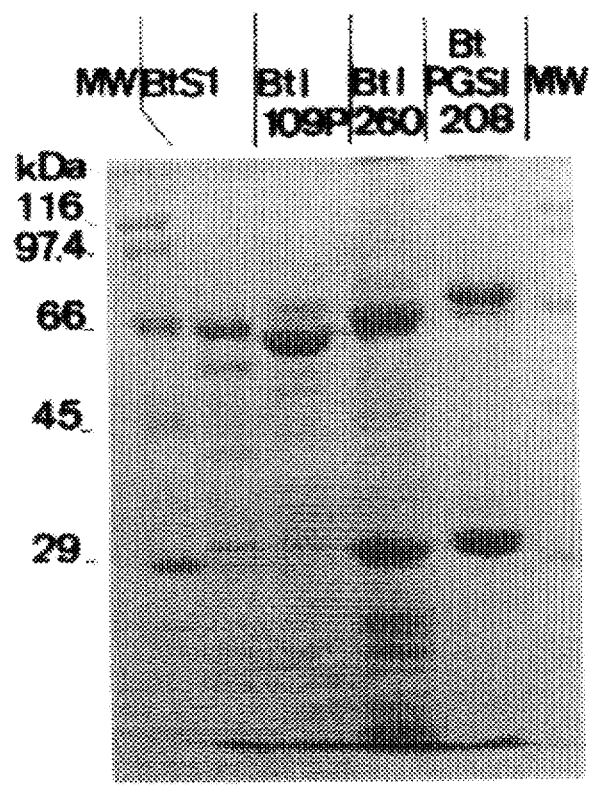
FIG. 1 shows the total protein patterns by SDS-PAGE of sporulated BtI109P, BtI260, BtS1 and BtPGSI208 Bacillus cultures.

In accordance with this invention, the BtI109P and BtI260 protoxins can be isolated in a conventional manner from, respectively, the BtI109P strain, deposited at the DSM under accession number 5870, and the BtI260 strain, deposited at the DSM under accession number 5871. For example, the BtI109P and BtI260 crystals can be isolated from sporulated cultures of their respective strains (Mahillon and Delcour, 1984), and then, the respective protoxins can be isolated from these crystals according to the method of Höfte et al (1986). The protoxins can be used to prepare monoclonal or polyclonal antibodies specific for these protoxins in a conventional manner (Höfte et al, 1988). The BtI109P toxin can then be obtained by protease digestion (e.g., by trypsin digestion) of the BtI109P protoxin. The BtI260 toxin can be obtained by protease digestion (e.g., by trypsin digestion) of the BtI260 protoxin.

The btI109P and btI260 genes can also be isolated from their respective strains in a conventional manner. For example, the btI109P or btI260 gene can be identified in its respective BtI109P or BtI260 strain, using the procedure described in U.S. patent application Ser. No. 821,582 and in EPA 86300291.1 and EPA 88402115.5 (which are incorporated herein by reference). Preferably, the btI109P and btI260 genes are each identified by: digesting total DNA from their respective BtI109P and BtI260 strains with one or more restriction enzymes; size fractionating the DNA fragments, so produced, into DNA fractions of 5 to 10 Kb; ligating such fractions to cloning vectors; transforming E. coli with the cloning vectors; and screening the clones with a suitable DNA probe. The DNA probe can be constructed: 1) from a highly conserved region of a bt gene which encodes another crystal protoxin against Coleoptera such as: the bt13 gene described in EPA 88402115.5 and by Höfte et al (1987); or 2) on the basis of the N-terminal amino acid sequence of the protoxin encoded by the respective btI109P or btI260 gene, which sequence can be determined by gas-phase sequencing of the immobilized protoxin (EPA 88402115.5).

Alternatively, the 5 to 10 kB fragments, prepared from total DNA of the BtI109P or BtI260 strain, can be ligated in suitable expression vectors and transformed in E. coli. The clones can then be screened by conventional colony immunoprobing methods (French et al, 1986) for expression of the BtI109P or BtI260 toxin with monoclonal or polyclonal antibodies raised against the toxin.

The so-identifed btI109P and btI260 genes can then each be sequenced in a conventional manner (Maxam and Gilbert, 1980) to obtain the DNA sequences. Hybridizations in Southern blots indicate that these genes are different from previously described genes encoding protoxins and toxins with activity against Coleoptera (Höfte and Whiteley, 1989).

An insecticidally effective part of each of the genes, encoding an insecticidally effective portion of its protoxin, and a truncated part of each of the sequenced genes, encoding Just its toxin, can be made in a conventional manner from each gene after the gene has been sequenced. The amino acid sequences of the BtI109P and BtI260 protoxins and toxins can further be determined from the DNA sequences of their respective btI109P and btI260 genes and truncated btI109P and btI260 genes. By "an insecticidally effective part" or "a part" of the btI109P or btI260 gene is meant a DNA sequence encoding a polypeptide which has fewer amino acids then the respective BtI109P or BtI260 protoxin but which is still toxic to Coleoptera. Such a part of the btI109P or btI260 gene can encode a BtI109P or BtI260 protoxin which has been truncated towards at least one trypsin cleavage site of the protoxin (U.S. patent application Ser. No. 821,582; EPA 86300291.1).

In order to express all or an insecticidally effective part of the btI109P or btI260 gene in *E. coli* and in plants, suitable restriction sites can be introduced, flanking each gene or gene part. This can be done by site directed mutagenesis, using well-known procedures (Stanssens et al, 1987; Stanssens et al, 1989).

The insecticidally effective btI109P or btI260 gene part, encoding an insecticidally effective portion of its respective BtI109P or BtI260 protoxin, can be stably inserted in a conventional manner into the nuclear genome of a single plant cell, and the so-transformed plant cell be used in a conventional manner to produce a transformed plant that is insect-resistant. In this regard, a disarmed Ti-plasmid, containing the insectidicidally effective btI109P or btI260 gene part, in *Agrobacterium tumefaciens* can be used to transform the plant cell, and thereafter, a transformed plant can be regenerated from the transformed plant cell using the procedures described, for example, in EP 116,718 and EP 270,822, PCT publication WO 84/02,913, EPA 87400544.0 and Gould et al. (1991) (which are also incorporated herein by reference). Preferred Ti-plasmid vectors each contain the insecticidally effective btI109P or btI260 gene part between the border sequences, or at least located to the left of the right border sequence, of the T-DNA of the Ti-plasmid. Of course, other types of vectors can be used to transform the plant cell, using procedures such as direct gene transfer (as described, for example, in EP 233,247), pollen mediated transformation (as described, for example, in EP 270,356, PCT publication WO 85/01856, and U.S. Pat. No. 4,684,611), plant RNA virus-mediated transformation (as described, for example, in EP 67,553 and U.S. Pat. No. 4,407,956), liposome-mediated transformation (as described, for example, U.S. Pat. No. 4,536,475), and other methods such as the recently described methods for transforming certain lines of corn (Fromm et al, 1990; Gordon-Kamm et al, 1990).

The resulting transformed plant can be used in a conventional plant breeding scheme to produce more transformed plants with the same characteristics or to introduce the insecticidally effective btI109P or btI260 gene part in other varieties of the same or related plant species. Seeds, which are obtained from the transfomed plants, contain the insecticidally effective btI109P or btI260 gene part as a stable genomic insert. Cells of the transformed plant can be cultured in a conventional manner to produce the insecticidally effective portion of the respective BtI109P or BtI260 protoxin, preferably the respective BtI109P or BtI260 toxin, which can be recovered for use in conventional insecticide compositions against Coloptera (U.S. patent application Ser. No. 821,582; EPA 86300291.1.).

The insecticidally effective btI109P or btI260 gene part, preferably the truncated btI109P or btI260 gene, is inserted in a plant cell genome so that the inserted part of the gene is downstream (i.e., 3') of, and under the control of, a promoter which can direct the expression of the gene part in the plant cell. This is preferably accomplished by inserting the btI109P or btI260 chimaeric gene in the plant cell genome. Preferred promoters include: the strong constitutive 35S promoters (the "35S promoters") of the cauliflower mosaic virus of isolates CM 1841 (Gardner et al, 1981), CabbB-S (Franck et al, 1980) and CabbB-JI (Hull and Howell, 1987); and the TR1' promoter and the TR2' promoter (the "TR1' promoter" and "TR2' promoter", respectively) which drive the expression of the 1' and 2' genes, respectively, of the T-DNA (Velten et al, 1984). Alternatively, a promoter can be utilized which is not constitutive but rather is specific for one or more tissues or organs of the plant (e.g., leaves and/or roots) whereby the inserted btI109P or btI260 gene part is expressed only in cells of the specific tissue(s) or organ(s). For example, the btI109P or btI260 gene part could be selectively expressed in the leaves of a plant (e.g., potato, corn, oilseed rape and rice) by placing the gene part under the control of a light-inducible promoter such as the promoter of the ribulose-1,5-bisphosphate carboxylase small subunit gene of the plant itself or of another plant such as pea as disclosed in U.S. patent application Ser. No. 821,582 and EPA 86300291.1. Another alternative is to use a promoter whose expression is inducible (e.g., by temperature or chemical factors).

The insecticidally effective btI109P or btI260 gene part is inserted in the plant genome so that the inserted part of the gene is upstream (i.e., 5') of suitable 3' end transcription regulation signals (i.e., transcript formation and polyadenylation signals). This is preferably accomplished by inserting the btI109P or btI260 chimaeric gene in the plant cell genome. Preferred polyadenylation and transcript formation signals include those of the octopine synthase gene (Gielen et al, 1984) and the T-DNA gene 7 (Velten and Schell, 1985), which act as 3'-untranslated DNA sequences in transformed plant cells.

It is preferred that the insecticidally effective btI109P or btI260 gene part be inserted in the plant genome in the same transcriptional unit as, and under the control of, the same promoter as a selectable marker gene. The resulting hybrid btI109P or btI260-marker gene will, thereby, be expressed in a transformed plant as a fusion protein (U.S. patent application Ser. No. 821,582; EPA 86300291.1; Vaeck et al, 1987). This result can be preferably accomplished by inserting a btI109P or btI260 chimaeric gene, containing the marker gene, in the plant cell genome. Any conventional marker gene can be utilized, the expression of which can be used to select transformed plant cells. An example of a suitable selectable marker gene is an antibiotic resistance gene such as the neo gene coding for kanamycin resistance (Reiss et al, 1984; EPA 87400544.0; U.S. patent application Ser. No. 821,582; EPA 86300291.1). Thereby, the insecticidally effective btI109P or btI260 gene part and the marker gene (e.g., the btI109P-neo or btI260-neo hybrid gene) are expressed in a transformed plant as a fusion protein (U.S. patent application Ser. No. 821,582; EPA 86300291.1; Vaeck et al, 1987).

All or an insecticidally effective part of the btI109P and btI260 genes, encoding Coleopteran toxins, can also be used to transform gram-positive bacteria, such as a *B. thuringiensis* which has insecticidal activity against Lepidoptera or Coleoptera. Thereby, a transformed Bt strain can be produced which is useful for combatting both Lepidopteran and Coleopteran insect pests or combatting additional Coleopteran insect pests. Transformation of a bacteria with all or part of the btI109P or btI260 gene, incorporated in a suitable cloning vehicle, can be carried out in a conventional manner, preferably using conventional electroporation techniques as described in PCT patent application PCT/EP89/01539, filed Dec. 11, 1989.

The BtI109P or BtI260 strain also can be transformed with all or an insecticidally effective part of one or more foreign Bt genes such as: the bt2 gene (U.S. patent application Ser. No. 821,582; EPA 86300291.1) or another Bt gene coding for all or an insecticidally effective portion of a Bt protoxin active against Lepidoptera; and/or the bt13 gene (EPA 88402115.5) or another Bt gene, such as the btPGSI208 gene or btPGSI245 gene (EPA 89400428.2; PCT publication WO 90/09445), coding for all or an insecticidally effective portion of a Bt protoxin active against Coleoptera. Thereby, a transformed Bt strain can be produced which is useful for combatting an even greater variety of insect pests, e.g., Lepidoptera and/or additional Coleoptera. Transformation of the BtI109P or BtI260 strain with all or part of a foreign Bt gene, incorporated in a conventional cloning vector, can be carried out in a well known manner, preferably using conventional electroporation techniques (Chassy et al, 1988).

Each of the BtI109P and BtI260 strains can be fermented by conventional methods (Dulmage, 1981) to provide high yields of cells. Under appropriate conditions which are well understood (Dulmage, 1981), the BtI109P and BtI260 strains each sporulate to provide their respective BtI109P and BtI260 crystal proteins in high yields.

The BtI109P and BtI260 strains, crystals, protoxins, toxins and/or insecticidally effective portions, preferably their protoxins, can each be used as the active ingredient in an insecticide composition used to control insect pests belonging to the order of Coleoptera. For example, the BtI109P or BtI260 crystals can be isolated from sporulated cultures of the BtI109P or BtI260 strain (Mahillon and Delcour, 1984), and then, the respective protoxin can be isolated from these crystals according to the method of Höfte et al (1986).

An insecticidal, particularly anti-Coleopteran, composition of this invention can be formulated in a conventional manner using the BtI109P or BtI260 strain or preferably its respective crystals, crystal proteins, protoxin, toxin and/or insecticidally effective portion of its protoxin as active ingredient(s), together with suitable carriers, diluents, emulsifiers and/or dispersants. This insecticide composition can be formulated as a wettable powder, pellets, granules or dust or as a liquid formulation with aqueous or non-aqueous solvents as a foam, gel, suspension, concentrate, etc. The concentration of the BtI109P or BtI260 strain, crystals, crystal proteins, protoxin, toxin and/or insecticidally effective protoxin portion in such a composition will depend upon the nature of the formulation and its intended mode of use. Generally, an insecticide composition of this invention can be used to protect a potato field for 2 to 4 weeks against Coleoptera with each application of the composition. For more extended protection (e.g., for a whole growing season), additional amounts of the composition should be applied periodically.

A method for controlling insects, particularly Coleoptera, in accordance with this invention preferably comprises applying (e.g., spraying), to a locus (area) to be protected, an insecticidal amount of the BtI109P or BtI260 crystals, crystal proteins, protoxin, toxin or insecticidally effective protoxin portion, preferably protoxin. The locus to be protected can include, for example, the habitat of the insect pests or growing vegetation or an area where vegetation is to be grown.

To obtain the BtI109P or BtI260 protoxin or toxin, cells of the BtI109P or BtI260 strain can be grown in a conventional manner on a suitable culture medium and then lysed using conventional means such as enzymatic degradation or detergents or the like. The protoxin can then be separated and purified by standard techniques such as chromatography, extraction, electrophoresis, or the like. The toxin can then be obtained by trypsin digestion of the protoxin.

The BtI109p or BtI260 cells also can be harvested and then applied intact, either alive or dead, preferably dried, to the locus to be protected. In this regard, it is preferred that a purified BtI109P or BtI260 strain (either alive or dead) be used, particularly a cell mass that is 90.0 to 99.9% BtI109P or BtI260 strain.

The BtI109P or BtI260 cells, crystals, crystal proteins, protoxin, toxin, or insecticidally effective protoxin portion can be formulated in an insecticidal composition in a variety of ways, using any number of conventional additives, wet or dry, depending upon the particular use. Additives can include wetting agents, detergents, stabilizers, adhering agents, spreading agents and extenders. Examples of such a composition include pastes, dusting powders, wettable powders, granules, baits and aerosol compositions. Other Bt cells, crystals, crystal proteins, protoxins, toxins, and insecticidally effective protoxin portions and other insecticides, as well as fungicides, biocides, herbicides and fertilizers, can be employed along with the BtI109P or BtI260 cells, crystals, crystal proteins, protoxin, toxin and/or insecticidally effective protoxin portion to provide additional advantages or benefits. Such an insecticidal composition can be prepared in a conventional manner, and the amount of the BtI109P or BtI260 cells, crystals, crystal proteins, protoxin, toxin, and/or insecticidally effective protoxin portion employed depends upon a variety of factors, such as the insect pest targeted, the composition used, the type of area to which the composition is to be applied, and the prevailing weather conditions. Generally, the concentration of the BtI109P or BtI260 protoxin, insecticidally effective protoxin portion and/or toxin will be at least about 0.1% of the weight of the formulation to about 100% by weight of the formulation, more often from about 0.15% to about 0.8% weight percent of the formulation.

In practice, some insects can be fed the BtI109P or BtI260 protoxin, toxin, insecticidally effective protoxin portion or mixtures thereof in the protected area, that is, in the area where such protoxin, toxin and/or insecticidally effective protoxin portion have been applied. Alternatively, some insects can be fed intact and alive cells of the BtI109P or BtI260 strain or transformants thereof, so that the insects ingest some of the strain's protoxin and suffer death or damage.

The following Examples illustrate the invention. The Figures and Sequence Listing, referred to in the Examples, are as follows:

Figures

FIG. 1—Total protein patterns by SDS-PAGE of sporulated BtI109P, BtI260, BtS1 and BtPGSI208 Bacillus cultures. "MW" designates molecular weight markers.

Figure 2:
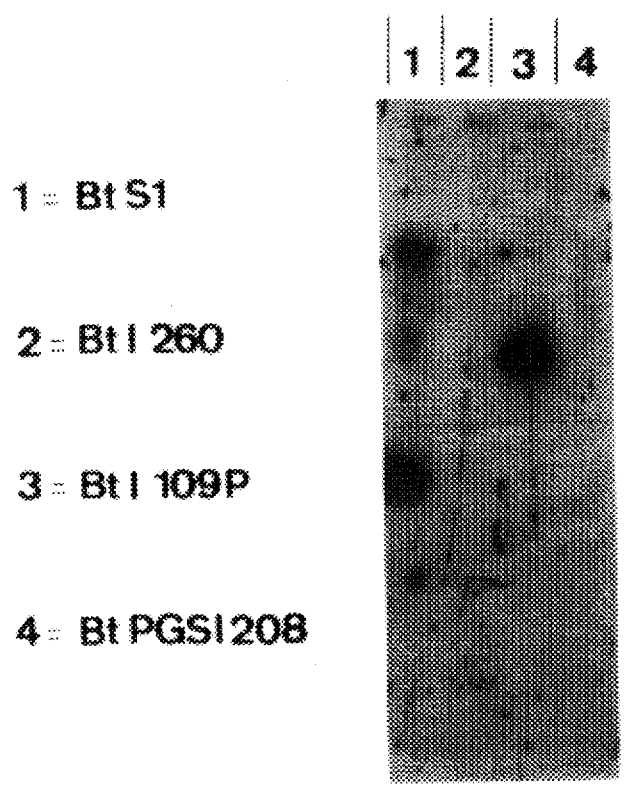
FIG. 2 shows the hybridization patterns under low stringency conditions of EcoRI digested total DNA prepared from strains BtS1, BtPGSI208, BtI109P and BtI260 with a PstI-EcoRV fragment of the genome of the BtS1 strain.

FIG. 2—Hybridisation pattern under low stringency conditions of EcoRI digested total DNA prepared from strains BtS1, BtPGSI208, BtI109P and BtI260 with a 1.46 kb PstI-EcoRV fragment of the genome of the BtS1 strain, containing an internal fragment of the bt13 gene ("cryIIIA" gene) as probe.

Figure 3:
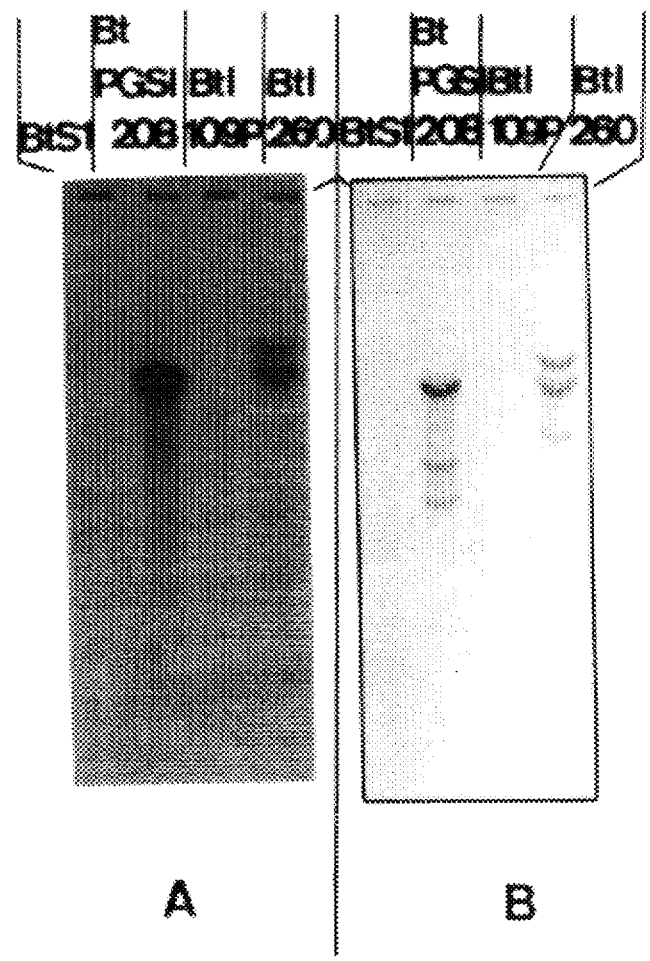
FIGS. 3A-B show the hybridization pattern under low stringency conditions of NlaIV digested total DNA prepared from strains BtS1, BtPGSI208, BtI109P and BtI260 with a 1.38 kb EcoRV-NcoI fragment of the genome of the BtPGSI208 strain.

FIG. 3—Hybridisation pattern under low stringency conditions of NlaIV digested total DNA prepared from strains BtS1, BtPGSI208, BtI109P and BtI260 with a 1.38 kb EcoRV-NcoI fragment of the genome of the BtPGSI208 strain, containing an internal fragment of the btPGSI208 gene ("cryIIIB" gene), as probe. Probe fragments were labeled with $^{32}$P (A) or with digoxygenin (B) (Boehringer Non-Radioactive Labeling Kit).

Sequence Listing

Seq. Id. No.1—DNA sequence of the btI109P gene. The derived aminoacid sequence of the encoded BtI109P protoxin is presented beneath the DNA sequence. The truncated btI109P gene, coding just for the BtI109P toxin, appears to extend from nucleotide position 397 to the TAA termination codon at nucleotide position 2179.

Seq. Id. No.2—Partial DNA sequence of the btI260 gene. The derived partial aminoacid sequence of the encoded BtI260 protoxin is presented beneath the DNA sequence.

Unless otherwise stated in the Examples, all procedures for making and manipulating recombinant DNA are carried out by the standardized procedures described in Maniatis et al, *Molecular Cloning—A laboratory Manual,* Cold Spring Harbor Laboratory (1982).

EXAMPLE 1

Characterization of the BtI109P and BtI260 strains.

The BtI109P strain was isolated from grain dust sampled in the Philippines and was deposited at the DSM on Apr. 4, 1990 under accession No. 5870.

The BtI260 strain was isolated from bat dung sampled in the Philippines and was deposited at the DSM on Apr. 4, 1990 under accession No. 5871.

Each strain can be cultivated on conventional standard media, preferably LB medium (Bacto-tryptone 10 g/l, yeast extract 5 g/l, NaCl 10 g/l and agar 15 g/l), preferably at 28° C. For long term storage, it is preferred to mix an equal volume of a spore-crystal suspension with an equal volume of 50% glycerol and store this at −70° C or lyophilize a spore suspension. For sporulation, the use of $T_3$ medium (tryprone 3 g/l, tryptose 2 g/l, yeast extract 1.5 g/l, 5 mg $MnCl_2$, 0.05M $Na_2PO_4$, pH 6.8 and 1.5% agar) is preferred for 24 hours at 28° C., followed by storage at 4° C. During its vegetative phase, each of the BtI109P and BtI260 strains can also grow under facultative anaerobic conditions, but sporulation only occurs under aerobic conditions.

Sterilization of each strain occurs by autoclave treatment at 120° C. (1 bar pressure) for 20 minutes. Such treatment totally inactivates the spores and the crystalline BtI109P and BtI260 protoxins. UV radiation (254 nm) inactivates the spores but not the protoxins.

After cultivating on Nutrient Agar ("NA", Difco Laboratories, Detroit, Mich., USA) for one day, colonies of each of the BtI109P and BtI260 strains form opaque white colonies with irregular edges. Cells of each strain (Gram positive rods of 1.7–2.4×5.6–7.7 230 m) sporulate after three days cultivation at 28° C. on NA. The crystal proteins produced during sporulation are packed in flat square crystals in the BtI109P strain and in small rhomboid crystals in the BtI260 strain. Both strains were further characterized by serotyping with *B. thuringiensis* H antisera (by B. de Barjac of Institut Pasteur, France). BtI109P belongs to serotype H 303b, at an agglutination titre of 25,000 with Bt kurstaki. BtI260 belongs to serotype H18, at an agglutination titre of 3,200 with Bt kumamotoensis.

EXAMPLE 2

Characteristics of the BtI109P and BtI260 crystals

The BtI109P and BtI260 strains were grown for 48 to 72 hours at 28° C. on $T_3$ medium. After sporulation, the spores and crystals were harvested in phosphate buffered saline solution ("PBS" from Oxoid Ltd., Basingstroke, Hampshire, U.K.). The resulting aqueous spore-crystal suspensions were centrifuged, and the pellets were resuspended in PBS, recentrifuged and the pellet resuspended again.

The total protein patterns of the sporulated cultures of BtI109P and BtI260 strains were compared (FIG. 1) to other Bacillus strains, which produce the CryIIIA or CryIIIB crystal proteins, according to Lambert et al (1987). For this comparison, an aliquot of the washed spore-crystal mixture of each strain was centrifuged, the supernatant discarded and the pellet solubilized in Sample Buffer Mix. The extracts containing crystal proteins, were analyzed on a 12.5% SDS-PAGE gel (Laemmli, 1970) and stained with Coomassie brilliant blue R-250. The results of this analysis revealed the presence of a major band (molecular weight 65.5 kDa) and two minor bands (MW. 72.4 kDa and 49.1 kDa) in spore-crystals of strain BtI109P and two major bands of about 65 kDa and a band of about 30 kDa in spore-crystals of strain BtI260. Furthermore, the overall protein patterns of BtI109P and BtI260 are clearly different from the overall protein pattern of BtS1.

EXAMPLE 3

Insecticidal activity of the BtI109P and BtI260 crystal proteins

As in Example 2, both strains were grown for 48 to 72 hrs at 28° C. on $T_3$ medium. After sporulation, the spores and crystals were harvested in PBS (phosphate buffered saline). The resulting spore-crystal suspensions were centrifuged, and the pellets were resuspended, recentrifuged and the pellets again resuspended after removal of the supernatant. The pellets were incubated overnight in aqueous solutions containing 50 mM $Na_2CO_3$ and 5 mM dithiotreitol. After centrifugation, the supernatants were recovered, and the protein contents of the extracts of the respective crystal proteins of the two strains were determined.

Potato leaves were dipped either in standardized sporecrystal mixtures or in aqueous dilutions of the crystal protein solutions and then air dried for two hours. Colorado potato beetle larvae of the first instar were placed on the treated leaves, and mortality of the larvae was determined after three days. These results were compared with the mortality of larvae fed leaves treated with either spore-crystal mixtures or solubilized crystal proteins of BtS1 (from DSM, accession no. 4288) which was used as a reference strain. LC50 (50% lethal concentration), expressed either as ug of solubilized crystal proteins/ml solution or as the number of spore-crystals in the dip-suspension, was calculated by Probit analysis (Finney, 1971). The results, including the 95% confidence interval and the slope of the probit line, are summarized in Tables 1 and 2, below.

TABLE I

Comparison of the toxicity of solubilized crystal proteins from the BtI109P strain, the BtI260 strain, the Bt San Diego strain (NRRL accession no. B-15939) and the BtS1 strain (reference strain) against larvae of *Leptinotarsa decemlineata.*

| Strain | LC50 ug/cm² | FL95min | FL95max | Slope |
| --- | --- | --- | --- | --- |
| BtI109P | 0.71 | 0.52 | 0.97 | 3.49 |
| BtI260 | 6.76 | 4.71 | 9.71 | 2.10 |
| BtS1 | 3.56 | 2.01 | 6.32 | 1.10 |
| Bt SAN DIEGO | 0.90 | 0.8 | 1.5 | 1.0 |

TABLE 2

Comparison of the toxicity of spore-crystal mixtures from the BtI109P strain, the BtI260 strain and the BtS1 strain (reference strain) against larvae of *Leptinotarsa decemlineata*.

| Strain | LC50 10⁶ spore crystals/ml | FL95min | FL95max | Slope |
|---|---|---|---|---|
| BtI109P | 5.78 | 4.06 | 8.24 | 3.07 |
| BtS1 | 3.24 | 2.37 | 4.42 | 4.18 |
| BtI260 | 68.6 | 48.6 | 99.9 | 3.2 |
| BtS1 | 8.5 | 6.2 | 11.4 | 4.9 |

EXAMPLE 4

Identification of the btI109P and btI260 genes

The BtI109P and BtI260 protoxins from the BtI109P and BtI260 strains respectively were detected by ELISA (Engvall and Pesce, 1978) with a polyclonal antiserum against the Bt13 coleopteran toxin (Höfts et al, 1987). The btI109P and btI260 genes were identified in their respective strains by preparing total DNA of these strains and then digesting the DNA with the restriction enzymes NlaIV and EcoRI.

The EcoRI-digested DNA was analyzed by Southern blotting, probing with a $^{32}$P labeled 1.46 kb. PstI-EcoRV fragment from the genome of the BtS1 strain (EPA 88402115.5) containing the bt13 gene. After hybridization with the probe, the blot was washed under low stringency conditions (2×SSC, 0.1% SDS at 68° C. for 2×15 min) and developed. The autoradiogram (FIG. 2) shows that only the btI109P gene is related to the bt13 gene. The hybridization pattern with the probe also showed that the btI109P gene was clearly different from the bt13 gene and that the genome of the BtI260 strain did not contain DNA sequences that are related to the PstI-EcoRV probe fragment of bt13 (cryIIIA) under the experimental conditions used. (FIG. 2)

The NlaIV-digested DNA was analyzed by Southern blotting, probing with $^{32}$P-labeled or digoxygenin (Non-Radioactive Labeling Kit, Boehringer Mannheim, Mannheim, Germany) 1.38 kb EcoRV-NcoI fragment from the genome of the BtPGSI208 strain (PCT patent application PCT/EP90/00244) containing the btPGSI208 or cryIIIB gene. After hybridization with the probe, the blot was washed under low stringency conditions (2×SSC, 0.1% SDS at 68° C. for 2×15 min) and developed. The results (FIG. 3) show that only the btI260 gene is related to the btPGSI208 gene. The hybridization pattern with the probe also showed that the btI260 gene was clearly different from the btPGSI208 gene and that the btI109P gene strain contains DNA sequences that are only distantly related to the btPGSI208 gene under the experimental conditions used (FIG. 3).

EXAMPLE 5

Cloning and expression of the btI109P gene

In order to isolate the btI109P gene, total DNA from the BtI109P strain was prepared. Subsequently, total DNA was digested with HindIII. The digested DNA was size fractionated on a sucrose gradient, and fragments ranging from 5 kb to 7 kb were ligated to the HindIII-digested and BAP-treated cloning vector pUC19 (Yanisch-Perron et al, 1985). Recombinant *E. coli* clones, "pUC.cryIIIDHd1", containing the vector were then screened with an internal 1.4 kb EcoRV-PstI DNA fragment of the bt13 gene (EP 305,275), as a probe, to identify clones containing the btI109P gene.

The so-identified DNA fragments were then sequenced (Seq. Id. No. 1) according to Maxam and Gilbert (1980).

Based on the analysis of its DNA sequence, the gene is cut with appropriate restriction enzymes to give the truncated btI109P gene, encoding the BtI109P toxin.

EXAMPLE 6

Cloning and expression of the btI260 gene

In order to isolate the btI260 gene, total DNA from the BtI260 strain is prepared and partially digested with Sau 3A. The digested DNA is size fractioned on a sucrose gradient and fragments ranging from 5 Kb to 10 Kb are ligated to the BglII-digested and BAP-treated cloning vector pECOR251 (deposited under accession no. 4711 at DSM). Recombinant *E. coli* clones are then screened with an internal NcoI-EcoRV DNA fragment of the btPGSI208 gene (EP 382,990), as a probe, to identify clones containing the btI260 gene.

DNA fragments containing the btI260 gene are then sequenced (Seq. Id. no. 2) according to Maxam and Gilbert (1980).

Based on the analysis of its DNA sequence, the gene is cut with appropriate restriction enzymes to give the truncated btI260 gene encoding the BtI260 toxin.

EXAMPLE 7

Construction of a btI109P-neo hybrid gene and a btI260-neo hybrid gene

Following the procedure of U.S. patent application Ser. No. 821,582 and EPA 88402115.5 and EPA 86300291.1, the truncated btI109P and btI260 genes from Examples 5 and 6 are each fused to the neo gene to form the corresponding hybrid gene.

EXAMPLE 8

Insertion of the btI109P and btI260 genes, the truncated btI109P and btI260 genes and the btI109P-neo and btI260-neo hybrid genes in *E. coli* and insertion of the truncated btI109P and btI260 genes and the btI109P-neo and btI260-neo hybrid genes in potato plants In order to express the btI109P gene and btI260 gene, the truncated btI109P gene and truncated btI260 gene, and the btI109P-neo hybrid gene and btI260-neo hybrid gene from Examples 5, 6 and 7 in *E. coli* and in plants, different gene cassettes are made in *E. coli* according to the procedures described in EPA 86300291.1 and EPA 88402115.5.

To allow major expression in plants, cassettes, each containing one of the truncated and/or hybrid genes, are each inserted in an intermediate plant expression vector (between the T-DNA border sequences of this vector), are each fused to transcript formation and polyadenylation signals in the plant expression vector, are each placed under the control of a constitutive promoter such as the promoter from cauliflower mosaic virus driving the 35S3 transcript (Hull and Howell, 1987) or the 2' promoter from the TR-DNA of the octopine Ti-plasmid (Velten et al, 1984), and are each fused to 3' end transcript formation and polyadenylation signals capable of acting in plants, such as the 3' end of the octopine synthase gene (Gielen et al, 1984).

Using standard procedures (Deblaere et al, 1985), the intermediate plant expression vectors, containing the truncated btI109P and btI260 genes and the btI109P-neo and btI260-neo hybrid genes, are transferred into the Agrobacterium strain C 58 Cl Rif$^R$ (U.S. patent application Ser. No. 821,582; EPA 86300291.1) carrying the disarmed Ti-plasmid pGV2260 (Vaeck et al, 1987). Selection for spectinomycin resistance yields cointegrated plasmids, consisting of pGV2260 and the respective intermediate plant expression vectors. Each of these recombinant Agrobacterium strains is then used to transform different potato plants (*Solanum tuberosum*) so that the truncated btI109P gene, the truncated btI260 gene, the btI109P-neo hybrid gene and the btI260-neo hybrid gene are contained in, and expressed by, different potato plant cells.

EXAMPLE 9

Expression of the truncated btI109P and btI260 genes and the btI109P-neo and btI260-neo hybrid genes in potato plants The insecticidal activity against Coleoptera of the expression products of the truncated btI109P and btI260 genes and the btI109P-neo and btI260-neo hybrid genes in leaves of transformed potato plants, generated from the transformed potato plant cells of Example 8, is evaluated by recording the growth rate and mortality of *Leptinotarsa decemlineata* larvae fed on these leaves. These results are compared with the growth rate of larvae fed leaves from untransformed potato plants. Toxicity assays are performed as described in EPA 88402115.5, U.S. patent application Ser. No. 821,582 and EPA 86300291.1. A significantly higher mortality rate is obtained among larvae fed on leaves of transformed potato plants containing the truncated btI109P gene, the truncated btI260 gene, the btI109P-neo hybrid gene or the btI260-neo hybrid gene than among larvae fed the leaves of untransformed plants.

Needless to say, this invention is not limited to the BtI109P (DSM 5870) strain and the BtI260 (DSM 5871) strain. Rather, the invention also includes any mutant or variant of the BtI109P or BtI260 strain which produces crystals, crystal proteins, protoxin or toxin having substantially the same properties, particularly insecticidal properties, as the BtI109P or BtI260 crystals, crystal proteins, protoxin or toxin. In this regard, variants of the BtI109P and BtI260 strains include variants whose total protein pattern is substantially the same as the protein pattern of either the BtI109P strain or the BtI260 strain as shown in FIG. 1.

This invention also is not limited to potato plants transformed with the truncated btI109P or btI260 gene. It includes any monocotyledonous or dicotyledonous plant, such as tomato, tobacco, rapeseed, alfalfa, sunflowers, cotton, corn, soybeans, brassicas, sugar beets and other vegetables, transformed with an insecticidally effective btI109P or btI260 gene part.

Nor is this invention limited to the use of *Agrobacterium tumefaciens* Ti-plasmids for transforming plant cells with an insecticidally effective btI109P or btI260 gene part. Other known techniques for plant cell transformations, such as by means of liposomes, by electropotation or by vector systems based on plant viruses or pollen, can be used for transforming monocotyledons and dicotyledons with such a gene part. For example, an insecticidally effective btI109P or btI260 gene part can be used to transform certain selected lines of corn and rice plants by methods such as are described by Fromm et al (1990), Gordon-Kamm et al (1990), Shimamoto et al (1989) and Datta et al (1990).

Furthermore, DNA sequences other than those present naturally in the BtI109P and BtI260 strains and encoding respectively the natural BtI109P and BtI260 protoxins, toxins and insecticidally effective protoxin portions can be used for transforming plants and bacteria. In this regard, the natural DNA sequence of these genes can be modified by: 1) replacing some codons with others that code either for the same amino acids or for other, preferably equivalent, amino acids; and/or 2) deleting or adding some codons; provided that such modifications do not substantially alter the properties, particularly the insecticidal properties, of the encoded BtI109P or BtII260 protoxin, the insecticidally effective portion of the BtI109P or BtI260 protoxin or the BtI109P or BtI260 toxin.

Also, other DNA recombinants containing the aforementioned DNA sequences in association with other foreign DNA, particularly the DNA of vectors suitable for transforming plants and microorganisms other than *E. coli*, are encompassed by this invention. In this regard, this invention is not limited to the specific plasmids containing the btI109P and btI260 genes, or parts thereof, that were heretofore described, but rather, this invention encompasses any DNA recombinants containing a DNA sequence that is their equivalent. Further, the invention relates to all DNA recombinants that include all or part of either the btI109P gene or the btI260 gene and that are suitable for transforming microorganisms (e.g., plant-associated bacteria such as *Bacillus subtilis*, Pseudomonas, and Xanthomonas or yeasts such as *Streptomyces cerevisiae*) under conditions which enable all or part of the gene to be expressed and to be recoverable from said microorganisms or to be transferred to a plant cell.

References

Chassy et al., Trends in Biotechnology 6, 303–309 (1988)

Datta S., Peterhans A., Datta K. and Potrykus I., Bio/Technology 8, 736–740 (1990).

Deblaere, R., Bijtebier, B. De Greve, H., Debock, F., Schell, J., Van Montagu, M. and Leemans, J., Nucleic Acids Research 13, 4777–4788 (1985).

Deblaere, R., Reynaerts A., Höfte H., Hernalsteens J. -P., Leemans J. and Van Montagu M., Methods in Enzymology 153, 277–292 (1988).

Dulmage, H. T., "Production of Bacteria for Biological Control of Insects" in *Biological Control in Crop Production*, Ed. Paparizas, D. C., Osmun Publishers, Totowa, N.J., USA, pp. 129–141 (1981).

Ellar, D. J., Knowles, B. H., Drobniewski, S. A. and Haider, M. Z., in "Fundamental and Applied aspects of Invertebrate Pathology". Ed. Samson, R. A., Vlak, J. M. and Peters, D. (1986) pp. 7–10. Wageningen, Foundation of the fourth International Colloqium of Invertebrate Pathology.

Engvall and Pesce, Scand. Immunol. Suppl. 7 (1978)

Finney, Probit Analysis, 3rd Edition, Cambridge University Press (1971)

Franck, Guilley, Jonard, Richards and Hirth, Cell 21, 285–294 (1980)

French, B. T., Maul, M N. and Maul, G. G., Anal. Biochem. 156, 417423 (1986)

Fromm M., Morrish F., Armstrong C., Williams R., Thomas J. and Klein T., Bio/Technology 8, 833–839 (1990).

Gardner, Howarth, Hahn, Brown-Luedi, Shepard and Messing, Nucleic Acids Research 9, 2871–2887 (1981)

Gielen, J., De Beukeleer, M., Seurinck, J., Deboeck, F., De Greve, H., Lemmers, M., Van Montagu, M. and Schell, J., EMBO J 3, 835–845 (1984).

Gordon-Kamm W., Spencer M., Mangano M., Adams T., Daines R., Start W., O'Brien J., Chambers S., Adams W., Willets N., Rice T., Mackey C., Krueger R., Kausch A. and Lemaux P., The Plant Cell 2, 603–618 (1990).

Gould et al., Plant Physiology 95, 426–434 (1991).

Höfte, H., De Greve, H., Seurinck, J., Jansens, S., Mahillon, J., Ampe, Vandekerckhove, J, Vanderbruggen, H., Van Montagu, M., Zabeau, M. and Vaeck, M., Eur. J. Biochem. 161, 273–280 (1986)

Höfte, H., Seurinck, J., Van Houtven A. and Vaeck, M., Nucleic Acids Research 15, 7183 (1987)

Höfte, H., Dissertation thesis at the State University of Ghent, Belgium (1988).

Höfte, H., Van Rie, J., Jansens, S., Van Houtven, A., Verbruggen, H. and Vaeck, M., Applied and Environmental Microbiology 54, 2010–2017 (1988)

Höfte H. and Whiteley H. R., Microbiological Review 53, 242–255 (1989).

Hull and Howell, Virology 86, 482–493 (1987)

Laemmli V., Nature 227, 680–685 (1970)

Lambert, B., Leyns, F., Van Rooyen, L., Gosselé, F., Papon, Y. and Swings, J. Applied and Environmental Microbiology 53, 1866–1871 (1987)

Mahillon, J. and Delcour, J., J. Microbiol. Methods 3, 69–73 (1984)

Maxam, A. M. and Gilbert, W., Methods in Enzymol. 65, 499–560 (1980).

Odell, J. T., Nagy, J., and Chua, N., Nature 313, 810–812 (1985).

Reiss, B., Sprengel, R., Will, H. and Schaller, H., Gene 30, 217–223 (1984).

Shimamoto K., Terada R., Izawa T. and Fujimoto H., Nature 338, 274–276 (1989).

Stanssens P., McKeown Y., Friedrich K. and Fritz H. J. (1988), "Oligonucleotide-directed construction of mutations by the gapped duplex DNA method using the pMA/c plasmid vectors", published in the collection of additional experimental procedures distributed at the EMBO laboratory course on "Directed mutagenesis and protein engineering" in July 1987 at the Max Planck Institute für Biochemie, Martinsried, Federal Republic of Germany.

Stanssens P., Opsomer C., McKeown Y., Kramer W., Zabeau M. and Fritz H. J., Nucleic Acids Research 12, 4441–4454 (1989).

Vaeck, M., Reynaerts, A., Höfte, M., Jansens, S., De Beuckeleer, M., Dean, C., Zabeau, M., Van Montagu, M. and Leemans, J., Nature 327, 33–37(1987).

Velten, J., Velten, L., Hain, R. and Schell, J., EMBO J 3, 2723–2730 (1984).

Velten, J. and Schell, J. Nucleic Acids Research 13, 6981–6998 (1985)

Yanisch-Perron, C., Vierra, J. and Messing, J., Gene33, 103–119 (1985).

---

We claim:

1. A transformed plant cell comprising a chimeric gene comprising an isolated DNA sequence encoding a BtI109P protein of SEQ. ID. No. 1; or an insecticidally effective part of the BtI109P protein of SEQ. ID. No. 1, or a truncated BtI109P protein of SEQ. ID. No. 1 having at least the toxin activity of the BtI109P protein, said DNA being under the control of a plant expressible promoter.

2. A plant or a seed thereof comprising the plant cell of claim 1.

3. A plant genome including, integrated therein, an isolated btI109P gene encoding a btI109P protein comprising the amino acid sequence of SEQ. ID. No. 1 or an insecticidally effective part of the BtI109P protein of SEQ. ID. No. 1 or a truncated BtI109P protein of SEQ. ID. No. 1 having at least the toxin activity of the BtI109P protein.

4. A plant tissue, the cells of which have the plant genome of claim 3.

5. A process for rendering a plant resistant to *Leptinotarsa decemlineata* comprising transforming a plant genome with an isolated btI109P gene encoding a btI109P protein comprising the amino acid sequence of SEQ ID No. 1 or an insecticidally effective part of the BtI109P protein of SEQ ID No. 1 or a truncated BtI109P protein of SEQ ID No. 1 having at least the toxin activity of the BtI109P protein of SEQ ID No. 1.

6. A process for transforming plants which comprises the steps of transforming plant cells with a DNA sequence encoding the protein of SEQ ID No. 1 or an insecticidally effective part thereof and regenerating said transformed plant cells into plants and reproduction material thereof comprising a DNA sequence encoding said protein or said insecticidally effective part.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2411 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: Bt109P (DSM accession number 5870)

( i x ) FEATURE:
( A ) NAME/KEY: CDS
( B ) LOCATION: 232..2190

( i x ) FEATURE:
( A ) NAME/KEY: misc_feature
( B ) LOCATION: 1..231
( D ) OTHER INFORMATION: /note="Nucleotides 1-231: 5'
( u p s t r e a m ) sequences of the btI109P gene (S)."

( i x ) FEATURE:
( A ) NAME/KEY: misc_feature
( B ) LOCATION: 2179..2411
( D ) OTHER INFORMATION: /note="Nucleotides 2179-2136: 3'
( d o w n s t r e a m ) sequences of the btI109P gene (S).
PROPERTIES: The btI109P gene codes for a 72 kD insecidal
crystal protein toxic to Coleoptera.

( x i ) SEQUENCE DESCRIPTION: SEQ ID NO:1:

```
CCTGTATATA ATATGCCAAT ACATTGTTAC AATTAATATT TAATCTAATG AAATGTTAAT        60

TATATATATA AATATATCTA TGATAAGTGC ATGAATAATT AAGTTTGAAA GGGGGGATGT       120

GTTAAAAGAA AGAATATTAA AATCTTGTGT TTGTACCGTC TAATGGATTT ATGGGAAATT       180

ATTTTATCAG ATTGAAAGTT ATGTATTATG ACAAGAAAGG GAGGAAGAAA A ATG AAT       237
                                                         Met Asn
                                                           1

CCG AAC AAT CGA AGT GAA CAT GAT ACA ATA AAA GCT ACT GAA AAT AAT        285
Pro Asn Asn Arg Ser Glu His Asp Thr Ile Lys Ala Thr Glu Asn Asn
          5                   10                  15

GAG GTA TCA AAT AAC CAT GCT CAA TAT CCT TTA GCA GAT ACT CCA ACA        333
Glu Val Ser Asn Asn His Ala Gln Tyr Pro Leu Ala Asp Thr Pro Thr
     20              25                  30

CTG GAA GAA TTA AAT TAT AAA GAG TTT TTA AGA AGG ACT ACA GAT AAT        381
Leu Glu Glu Leu Asn Tyr Lys Glu Phe Leu Arg Arg Thr Thr Asp Asn
 35              40                  45                      50

AAT GTG GAA GCA CTA GAC AGC TCA ACA ACA AAA GAT GCC ATT CAA AAA        429
Asn Val Glu Ala Leu Asp Ser Ser Thr Thr Lys Asp Ala Ile Gln Lys
                 55                  60                  65

GGG ATT TCC ATA ATA GGT GAT CTC CTA GGT GTA GTA GGT TTC CCA TAT        477
Gly Ile Ser Ile Ile Gly Asp Leu Leu Gly Val Val Gly Phe Pro Tyr
                 70                  75                  80

GGT GGA GCG CTT GTT TCT TTT TAT ACA AAC TTA TTA AAC ACT ATC TGG        525
Gly Gly Ala Leu Val Ser Phe Tyr Thr Asn Leu Leu Asn Thr Ile Trp
             85                  90                  95

CCA GGT GAA GAC CCT TTA AAG GCT TTT ATG CAA CAA GTA GAA GCA TTG        573
Pro Gly Glu Asp Pro Leu Lys Ala Phe Met Gln Gln Val Glu Ala Leu
100                 105                 110

ATA GAC CAG AAA ATA GCG GAT TAT GCG AAA GAT AAA GCA ACT GCA GAG        621
Ile Asp Gln Lys Ile Ala Asp Tyr Ala Lys Asp Lys Ala Thr Ala Glu
115                 120                 125                 130

TTA CAA GGA CTT AAA AAT GTT TTC AAA GAT TAT GTT AGT GCA TTG GAT        669
Leu Gln Gly Leu Lys Asn Val Phe Lys Asp Tyr Val Ser Ala Leu Asp
                135                 140                 145

TCA TGG GAC AAA ACT CCT TTG ACT TTA CGA GAT GGA CGA AGC CAA GGG        717
Ser Trp Asp Lys Thr Pro Leu Thr Leu Arg Asp Gly Arg Ser Gln Gly
                150                 155                 160

CGC ATA AGA GAG CTA TTT TCT CAA GCA GAA AGT CAT TTT CGT CGT TCA        765
Arg Ile Arg Glu Leu Phe Ser Gln Ala Glu Ser His Phe Arg Arg Ser
            165                 170                 175

ATG CCG TCG TTT GCA GTC TCT GGA TAC GAA GTT CTA TTT CTG CCA ACA        813
Met Pro Ser Phe Ala Val Ser Gly Tyr Glu Val Leu Phe Leu Pro Thr
        180                 185                 190

TAT GCA CAG GCC GCG AAC ACA CAT TTA TTA CTA TTA AAA GAC GCT CAA        861
Tyr Ala Gln Ala Ala Asn Thr His Leu Leu Leu Leu Lys Asp Ala Gln
195                 200                 205                 210

ATT TAT GGA ACG GAT TGG GGA TAT TCT ACA GAT GAT CTT AAT GAG TTT        909
Ile Tyr Gly Thr Asp Trp Gly Tyr Ser Thr Asp Asp Leu Asn Glu Phe
                215                 220                 225

CAC ACA AAA CAA AAG GAT CTT ACG ATA GAA TAT ACA AAT CAT TGT GCC        957
His Thr Lys Gln Lys Asp Leu Thr Ile Glu Tyr Thr Asn His Cys Ala
                230                 235                 240

AAA TGG TAT AAG GCA GGA TTA GAT AAA TTA AGA GGT TCG ACT TAT GAA       1005
Lys Trp Tyr Lys Ala Gly Leu Asp Lys Leu Arg Gly Ser Thr Tyr Glu
            245                 250                 255

GAG TGG GTA AAA TTT AAT CGT TAT CGC AGA GAG ATG ACA TTA ACA GTA       1053
Glu Trp Val Lys Phe Asn Arg Tyr Arg Arg Glu Met Thr Leu Thr Val
        260                 265                 270
```

-continued

| | | | | | | | | | | | | | | | | |
|---|---|---|---|---|---|---|---|---|---|---|---|---|---|---|---|---|
| TTA | GAT | TTA | ATT | ACG | CTG | TTT | CCA | TTG | TAT | GAT | GTT | CGA | ACA | TAC | ACT | 1101 |
| Leu | Asp | Leu | Ile | Thr | Leu | Phe | Pro | Leu | Tyr | Asp | Val | Arg | Thr | Tyr | Thr | |
| 275 | | | | 280 | | | | | | 285 | | | | | 290 | |
| AAA | GGA | GTT | AAA | ACT | GAA | TTA | ACA | AGA | GAC | GTT | TTA | ACT | GAT | CCA | ATT | 1149 |
| Lys | Gly | Val | Lys | Thr | Glu | Leu | Thr | Arg | Asp | Val | Leu | Thr | Asp | Pro | Ile | |
| | | | | 295 | | | | | 300 | | | | | 305 | | |
| GTT | GCC | GTC | AAC | AAT | ATG | AAT | GGC | TAT | GGA | ACA | ACC | TTC | TCT | AAT | ATA | 1197 |
| Val | Ala | Val | Asn | Asn | Met | Asn | Gly | Tyr | Gly | Thr | Thr | Phe | Ser | Asn | Ile | |
| | | | 310 | | | | | 315 | | | | | 320 | | | |
| GAA | AAT | TAT | ATC | CGA | AAA | CCG | CAT | CTA | TTT | GAC | TAT | TTG | CAT | GCG | ATT | 1245 |
| Glu | Asn | Tyr | Ile | Arg | Lys | Pro | His | Leu | Phe | Asp | Tyr | Leu | His | Ala | Ile | |
| | | 325 | | | | | 330 | | | | | 335 | | | | |
| CAA | TTT | CAC | TCG | CGC | TTA | CAA | CCT | GGA | TAT | TTT | GGA | ACG | GAC | TCT | TTC | 1293 |
| Gln | Phe | His | Ser | Arg | Leu | Gln | Pro | Gly | Tyr | Phe | Gly | Thr | Asp | Ser | Phe | |
| | 340 | | | | | 345 | | | | | 350 | | | | | |
| AAT | TAT | TGG | AGT | GGT | AAT | TAT | GTT | TCA | ACT | AGA | TCT | AGC | ATA | GGA | TCA | 1341 |
| Asn | Tyr | Trp | Ser | Gly | Asn | Tyr | Val | Ser | Thr | Arg | Ser | Ser | Ile | Gly | Ser | |
| 355 | | | | | 360 | | | | | 365 | | | | | 370 | |
| GAT | GAA | ATA | ATC | CGA | TCT | CCA | TTC | TAT | GGA | AAT | AAA | TCT | ACT | TTA | GAT | 1389 |
| Asp | Glu | Ile | Ile | Arg | Ser | Pro | Phe | Tyr | Gly | Asn | Lys | Ser | Thr | Leu | Asp | |
| | | | | 375 | | | | | 380 | | | | | 385 | | |
| GTT | CAA | AAT | TTA | GAA | TTT | AAC | GGG | GAA | AAA | GTC | TTT | AGA | GCT | GTA | GCA | 1437 |
| Val | Gln | Asn | Leu | Glu | Phe | Asn | Gly | Glu | Lys | Val | Phe | Arg | Ala | Val | Ala | |
| | | | 390 | | | | | 395 | | | | | 400 | | | |
| AAT | GGT | AAT | CTG | GCA | GTC | TGG | CCG | GTG | GGT | ACA | GGA | GGT | ACC | AAA | ATA | 1485 |
| Asn | Gly | Asn | Leu | Ala | Val | Trp | Pro | Val | Gly | Thr | Gly | Gly | Thr | Lys | Ile | |
| | | 405 | | | | | 410 | | | | | 415 | | | | |
| CAT | TCT | GGT | GTT | ACA | AAA | GTA | CAA | TTC | AGT | CAG | TAC | AAT | GAT | CGA | AAA | 1533 |
| His | Ser | Gly | Val | Thr | Lys | Val | Gln | Phe | Ser | Gln | Tyr | Asn | Asp | Arg | Lys | |
| | 420 | | | | | 425 | | | | | 430 | | | | | |
| GAT | GAA | GTA | AGA | ACA | CAA | ACG | TAT | GAC | TCA | AAA | AGA | AAT | GTT | GGT | GGT | 1581 |
| Asp | Glu | Val | Arg | Thr | Gln | Thr | Tyr | Asp | Ser | Lys | Arg | Asn | Val | Gly | Gly | |
| 435 | | | | | 440 | | | | | 445 | | | | | 450 | |
| ATC | GTC | TTT | GAT | TCC | ATT | GAT | CAA | TTG | CCT | CCA | ATA | ACA | ACA | GAT | GAA | 1629 |
| Ile | Val | Phe | Asp | Ser | Ile | Asp | Gln | Leu | Pro | Pro | Ile | Thr | Thr | Asp | Glu | |
| | | | | 455 | | | | | 460 | | | | | 465 | | |
| TCT | CTA | GAA | AAA | GCA | TAT | AGT | CAT | CAA | CTC | AAT | TAC | GTA | AGG | TGC | TTC | 1677 |
| Ser | Leu | Glu | Lys | Ala | Tyr | Ser | His | Gln | Leu | Asn | Tyr | Val | Arg | Cys | Phe | |
| | | | 470 | | | | | 475 | | | | | 480 | | | |
| TTA | TTG | CAG | GGT | GGA | AGA | GGA | ATA | ATC | CCA | GTG | TTT | ACT | TGG | ACA | CAT | 1725 |
| Leu | Leu | Gln | Gly | Gly | Arg | Gly | Ile | Ile | Pro | Val | Phe | Thr | Trp | Thr | His | |
| | | 485 | | | | | 490 | | | | | 495 | | | | |
| AAG | AGT | GTA | GAC | TTT | TAT | AAT | ACG | CTT | GAT | TCA | GAA | AAA | ATT | ACG | CAA | 1773 |
| Lys | Ser | Val | Asp | Phe | Tyr | Asn | Thr | Leu | Asp | Ser | Glu | Lys | Ile | Thr | Gln | |
| | 500 | | | | | 505 | | | | | 510 | | | | | |
| ATC | CCT | TTC | GTA | AAG | GCA | TTT | ATT | TTA | GTA | AAT | AGT | ACT | TCC | GTT | GTC | 1821 |
| Ile | Pro | Phe | Val | Lys | Ala | Phe | Ile | Leu | Val | Asn | Ser | Thr | Ser | Val | Val | |
| 515 | | | | | 520 | | | | | 525 | | | | | 530 | |
| GCA | GGT | CCT | GGA | TTC | ACA | GGC | GGA | GAC | ATA | ATA | AAA | TGT | ACG | AAT | GGA | 1869 |
| Ala | Gly | Pro | Gly | Phe | Thr | Gly | Gly | Asp | Ile | Ile | Lys | Cys | Thr | Asn | Gly | |
| | | | | 535 | | | | | 540 | | | | | 545 | | |
| TCT | GGA | TTA | ACT | TTA | TAT | GTT | ACA | CCG | GCA | CCG | GAC | TTG | ACG | TAT | TCT | 1917 |
| Ser | Gly | Leu | Thr | Leu | Tyr | Val | Thr | Pro | Ala | Pro | Asp | Leu | Thr | Tyr | Ser | |
| | | | 550 | | | | | 555 | | | | | 560 | | | |
| AAA | ACA | TAT | AAA | ATT | CGA | ATT | CGT | TAT | GCT | TCT | ACA | TCT | CAG | GTG | AGA | 1965 |
| Lys | Thr | Tyr | Lys | Ile | Arg | Ile | Arg | Tyr | Ala | Ser | Thr | Ser | Gln | Val | Arg | |
| | | 565 | | | | | 570 | | | | | 575 | | | | |
| TTT | GGA | ATT | GAC | TTA | GGC | AGT | TAC | ACT | CAT | AGT | ATT | TCG | TAT | TTC | GAT | 2013 |
| Phe | Gly | Ile | Asp | Leu | Gly | Ser | Tyr | Thr | His | Ser | Ile | Ser | Tyr | Phe | Asp | |
| 580 | | | | | 585 | | | | | 590 | | | | | | |

-continued

```
AAA ACG ATG GAT AAA GGA AAT ACA TTA ACG TAT AAT TCA TTT AAT TTA      2061
Lys Thr Met Asp Lys Gly Asn Thr Leu Thr Tyr Asn Ser Phe Asn Leu
595                 600                 605                 610

TCA AGT GTC AGC AGA CCA ATT GAA ATA TCA GGA GGG AAT AAA ATC GGG      2109
Ser Ser Val Ser Arg Pro Ile Glu Ile Ser Gly Gly Asn Lys Ile Gly
                615                 620                 625

GTA TCC GTC GGA GGT ATT GGC TCT GGG GAT GAA GTT TAT ATA GAC AAA      2157
Val Ser Val Gly Gly Ile Gly Ser Gly Asp Glu Val Tyr Ile Asp Lys
            630                 635                 640

ATC GAA TTT ATT CCA ATG GAT TAA ATT TTA CTA AAGAGCTAGT ATTAACCACT    2210
Ile Glu Phe Ile Pro Met Asp  *  Ile Leu Leu
        645                 650

TAGGATAATA AGAATCGGGT ACAAAAGTAA GTTTATAAAA TGAATAAAAC AGTGTTCTTC    2270

ATCCTTCGCT TTTTGAAGGT AGACAAAGAA CACTGTTTTT ACTTTTAGAA TAAATATTTT    2330

TTGTGTAATC ACATAAAGGG AGCAAAGAAA GTAGGGATAT GTCACTAGCA ATTAGAATTA    2390

GTAGATCCAG TAAGTAATTA A                                              2411
```

( 2 ) INFORMATION FOR SEQ ID NO:2:

( i ) SEQUENCE CHARACTERISTICS:
( A ) LENGTH: 1291 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: BtI260 (DSM accession number 5871)

( i x ) FEATURE:
( A ) NAME/KEY: CDS
( B ) LOCATION: 2..1045

( i x ) FEATURE:
( A ) NAME/KEY: misc_feature
( B ) LOCATION: 2..1045
( D ) OTHER INFORMATION: /note="Nucleotides 2-1045: 5'end of the btI260 gene coding for the C-terminal end of the BTI260 insecticidal protein (numbering of ( i x ) FEATURE:
( A ) NAME/KEY: misc_feature
( B ) LOCATION: 2..1045
( D ) OTHER INFORMATION: /note="PROPERTIES: The btI260 gene codes for a 66 kD insecticidal protein toxic to Coleoptera."

( x i ) SEQUENCE DESCRIPTION: SEQ ID NO:2:

```
G AAA GAT CCA ATT TTT TCA CTT AAT ACT CTT CAG GAG TAT GGA CCA          46
  Lys Asp Pro Ile Phe Ser Leu Asn Thr Leu Gln Glu Tyr Gly Pro
    1               5                  10                  15

ACT TTT TTG AGT ATA GAA AAC TCT ATT CGA AAA CCT CAT TTA TTT GAT        94
Thr Phe Leu Ser Ile Glu Asn Ser Ile Arg Lys Pro His Leu Phe Asp
                20                  25                  30

TAT TTA CAG GGG ATT GAA TTT CAT ACG CGT CTT CAA CCT GGT TAC TTT       142
Tyr Leu Gln Gly Ile Glu Phe His Thr Arg Leu Gln Pro Gly Tyr Phe
            35                  40                  45

GGG AAA GAT TCT TTC AAT TAT TGG TCT GGT AAT TAT GTA GAA ACT AGA       190
Gly Lys Asp Ser Phe Asn Tyr Trp Ser Gly Asn Tyr Val Glu Thr Arg
        50                  55                  60

CCT AGT ATA GGA TCT AGT AAG ACA ATT ACT TCC CCA TTT TAT GGA GAT       238
```

|          |          |          |          |          |          |          |          |          |          |          |          |          |          |          |      |
|----------|----------|----------|----------|----------|----------|----------|----------|----------|----------|----------|----------|----------|----------|----------|------|
| Pro      | Ser      | Ile      | Gly      | Ser      | Ser      | Lys      | Thr      | Ile      | Thr      | Ser      | Pro      | Phe      | Tyr      | Gly      | Asp  |
|          | 65       |          |          |          |          | 70       |          |          |          |          | 75       |          |          |          |      |

```
AAA TCT ACT GAA CCT GTA CAA AAG CTA AGC TTT GAT GGA CAA AAA GTT       286
Lys Ser Thr Glu Pro Val Gln Lys Leu Ser Phe Asp Gly Gln Lys Val
80              85              90              95

TAT CGA ACT ATA GCT AAT ACA GAC GTA GCG GCT TGG CCG AAT GGT AAG       334
Tyr Arg Thr Ile Ala Asn Thr Asp Val Ala Ala Trp Pro Asn Gly Lys
                100             105             110

GTA TAT TTA GGT GTT ACG AAA GTT GAT TTT AGT CAA TAT GAT GAT CAA       382
Val Tyr Leu Gly Val Thr Lys Val Asp Phe Ser Gln Tyr Asp Asp Gln
            115             120             125

AAA AAT GAA ACT AGT ACA CAA ACA TAT GAT TCA AAA AGA AAC AAT GGC       430
Lys Asn Glu Thr Ser Thr Gln Thr Tyr Asp Ser Lys Arg Asn Asn Gly
        130             135             140

CAT GTA AGT GCA CAG GAT TCT ATT GAC CAA TTA CCG CCA GAA ACA ACA       478
His Val Ser Ala Gln Asp Ser Ile Asp Gln Leu Pro Pro Glu Thr Thr
    145             150             155

GAT GAA CCA CTT GAA AAA GCA TAT AGT CAT CAG CTT AAT TAC GCG GAA       526
Asp Glu Pro Leu Glu Lys Ala Tyr Ser His Gln Leu Asn Tyr Ala Glu
160             165             170             175

TGT TTC TTA ATG CAG GAC CGT CGT GGA ACA ATT CCA TTT TTT ACT TGG       574
Cys Phe Leu Met Gln Asp Arg Arg Gly Thr Ile Pro Phe Phe Thr Trp
                180             185             190

ACA CAT AGA AGT GTA GAC TTT TTT AAT ACA ATT GAT GCT GAA AAG ATT       622
Thr His Arg Ser Val Asp Phe Phe Asn Thr Ile Asp Ala Glu Lys Ile
                195             200             205

ACT CAA CTT CCA GTA GTG AAA GCA TAT GCC TTG TCT TCA GGT GCT TCC       670
Thr Gln Leu Pro Val Val Lys Ala Tyr Ala Leu Ser Ser Gly Ala Ser
            210             215             220

ATT ATT GAA GGT CCA GGA TTC ACA GGA GGA AAT TTA CTA TTC CTA AAA       718
Ile Ile Glu Gly Pro Gly Phe Thr Gly Gly Asn Leu Leu Phe Leu Lys
        225             230             235

GAA TCT AGT AAT TCA ATT GCT AAA TTT AAA GTT ACA TTA AAT TCA GCA       766
Glu Ser Ser Asn Ser Ile Ala Lys Phe Lys Val Thr Leu Asn Ser Ala
240             245             250             255

GCC TTG TTA CAA CGA TAT CGT GTA AGA ATA CGC TAT GCT TCT ACC ACT       814
Ala Leu Leu Gln Arg Tyr Arg Val Arg Ile Arg Tyr Ala Ser Thr Thr
                260             265             270

AAC TTA CGA CTT TTT GTG CAA AAT TCA AAC AAT GAT TTT CTT GTC ATC       862
Asn Leu Arg Leu Phe Val Gln Asn Ser Asn Asn Asp Phe Leu Val Ile
                275             280             285

TAC ATT AAT AAA ACT ATG AAT AAA GAT GAT GAT TTA ACA TAT CAA ACA       910
Tyr Ile Asn Lys Thr Met Asn Lys Asp Asp Asp Leu Thr Tyr Gln Thr
            290             295             300

TTT GAT CTC GCA ACT ACT AAT TCT AAT ATG GGG TTC TCG GGT GAT AAG       958
Phe Asp Leu Ala Thr Thr Asn Ser Asn Met Gly Phe Ser Gly Asp Lys
        305             310             315

AAT GAA CTT ATA ATA GGA GCA GAA TCT TTC GTT TCT AAT GAA AAA ATC      1006
Asn Glu Leu Ile Ile Gly Ala Glu Ser Phe Val Ser Asn Glu Lys Ile
320             325             330             335

TAT ATA GAT AAG ATA GAA TTT ATC CCA GTA CAA TTG TAAGGAGATT           1052
Tyr Ile Asp Lys Ile Glu Phe Ile Pro Val Gln Leu
                340             345

TTAAAATGTT GGGTGATGGT CAAAATGAAA GAATAGGAAG GTGAATTTTG ATGGTTAGGA    1112

AAGATTCTTT TAACAAAAGC AACATGGAAA AGTATACAGT ACAAATATTA GAAATAAAAT    1172

TTATTAACAC AGGGGAAGAT GGTAAACCAG AACCGTATGG TTATATTGAC TTTTATTATC    1232

AACCTGCTCC TAACCTGAGA GAAGAAAAAG TAAGAATTTG GGAAGAGGAA AATAGTAGC     1291
```